United States Patent [19]

Vollmer et al.

[11] 4,118,590

[45] Oct. 3, 1978

[54] PHOSPHORBETAINES AND PROCESS FOR MAKING THEM

[75] Inventors: Hartfrid Vollmer, Erftstadt Liblar; Klaus Hestermann, Erftstadt Bliesheim, both of Fed. Rep. of Germany

[73] Assignee: Hoechst Aktiengesellschaft, Frankfurt am Main, Fed. Rep. of Germany

[21] Appl. No.: 736,092

[22] Filed: Oct. 27, 1976

Related U.S. Application Data

[63] Continuation-in-part of Ser. No. 721,087, Sep. 7, 1976, abandoned.

[30] Foreign Application Priority Data

Sep. 10, 1975 [DE] Fed. Rep. of Germany ....... 2540260

[51] Int. Cl.$^2$ ............................................. C07F 9/54
[52] U.S. Cl. .......................... 560/190; 260/45.85 T; 560/81; 560/125; 560/197; 560/198
[58] Field of Search ................. 260/485 G, 485 J; 560/190, 198, 81

[56] References Cited

U.S. PATENT DOCUMENTS 3,654,342   4/1972   Gillham et al. ................... 260/485 J

*Primary Examiner*—Jane S. Myers
*Attorney, Agent, or Firm*—Connolly and Hutz

[57] ABSTRACT

Production of novel phosphobetaines of general formula I

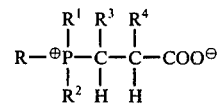

in which $R^1$ and $R^2$ each stand for organic groups having from 1 to 18 carbon atoms, and $R^1$ or $R^2$ may be identical with the substituent R, the substituent R being a radical of the general formula II

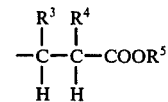

in which $R^3$ and $R^4$ each stand for organic groups having from 1 to 18 carbon atoms, and/or hydrogen atoms, and $R^5$ stands for a linear or branched alkyl group having from 1 to 4 carbon atoms, which may optionally have a halogen or hydroxylic group substituent attached thereto.

15 Claims, No Drawings

PHOSPHORBETAINES AND PROCESS FOR MAKING THEM

This application is a continuation-in-part application of application Ser. No. 721,087 filed Sept. 7, 1976 now abandoned.

The present invention relates to a novel group of phosphobetaines of the general formula I

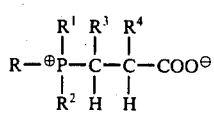

in which $R^1$ and $R^2$ each stand for linear and/or branched, identical or different alkyl-, cycloalkyl-, aryl-, alkylaryl-, and aralkyl groups having from 1 to 18, preferably 1 to 6, more preferably 1 or 2 carbon atoms, and $R^1$ or $R^2$ may be identical with the substituent R, the substituent R being a radical of the following general formula II

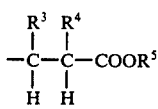

in which $R^3$ and $R^4$ each stand for linear and/or branched, identical and/or different alkyl-, cycloalkyl-, aryl-, alkylaryl-, and aralkyl groups having from 1 to 18, preferably 1 to 6 carbon atoms, and/or hydrogen atoms, and $R^5$ stands for a linear or branched alkyl group having from 1 to 4 carbon atoms, which may optionally have a halogen or hydroxylic group substituent attached thereto.

The invention also relates to a process for making the above phosphobetaines.

Phosphobetaines which contain ester groups in addition to the carboxylate group in the molecule have not been described heretofore.

The phosphobetaines described heretofore, in which the quaternary phosphonium ion is intramolecularly saturated by means of a carboxylate group, are high-melting stable compounds. As described in Houben-Weyl, Methoden der Organischen Chemie, vol. XII/1, page 107 et seq (Georg Thieme Verlag, Stuttgart, 1963), these phosphobetaines are formed by multiple stage reaction. Trimethylphosphine, for example, can be reacted with chloroacetic acid to give carboxymethyltrimethyl phosphonium chloride which can be converted to the corresponding phosphobetaine by treatment with moist silver oxide.

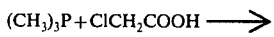

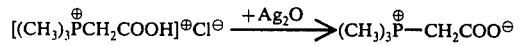

Phosphonium salts from tertiary phosphines and chloroacetic acid alkyl esters, which are admixed with basic media, give the corresponding phosphine alkylenes rather than phosphobetaines containing a carboxylate group.

A further process wherein trishydroxymethylphosphine is additively combined with an α,β-unsaturated carboxylic acid in accordance with the following reaction equation:

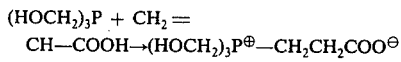

has been described in German Patent Specification No. 1,045,401.

Triphenylphosphine has been shown to form an analogous compound (cf. W. Hoffmann, Chem. Ber. 94, 1331-6 (1961)).

It has also been described that phosphobetaines of the following formula

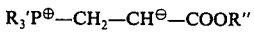

are obtained by reacting a tertiary phosphine with an α,β-unsaturated carboxylic acid ester. These, however, are unstable phosphobetaines which undergo further reaction with the resultant formation of polymers or phosphine alkylenes (M. A. Shaw and R. S. Ward, Topics in Phosphorus Chemistry, vol. 7, 1-35 (1972)). In effecting the same reaction L. Hörner, W. Jurgeleit and K. Klüfpel (cf. Liebigs Am. Chem. 591, 108-117 (1955)) obtained the corresponding polymeric products of α,β-unsaturated carboxylic acid esters. In other words, the tertiary phosphines were found to act as polymerization catalysts. The additive combination of the compounds with the resultant formation of a phosphobetaine containing a carboxylate group has not been described heretofore.

The processes described hereinabove for making phosphobetaines containing a carboxylate group are highly unsatisfactory inasmuch as they call for the exclusive use of tertiary phosphine starting materials, for which it is partially necessary to be first converted to phosphonium salts and for the phosphonium salts to be then subjected to alkaline treatment so as to obtain the desired product.

In addition to this, the prior art methods can only be used for making phosphobetaines into which the carboxylate is introduced via a carboxylic acid. α,β-unsaturated carboxylic acid alkyl esters have been found to react with tertiary phosphines to give phoshine alkylenes or polymers. Phosphobetaines containing a carboxylate group are not obtainable in this manner.

The present invention now unexpectedly provides a process for making a novel group of phosphobetaines of general formula I which comprises reacting one or more phosphines of general formula III

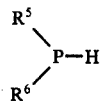

in which $R^5$ has the meaning given above, and $R^6$ has the same meaning as $R^4$ with the exception of hydrogen, with one or more α,β-unsaturated carboxylic acid esters of general formula IV

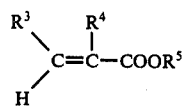

in which $R^3$, $R^4$ and $R^5$ equally have the meanings given hereinabove, the reaction being effected in a single stage in the presence of water or a solvent/water-mixture; and separating the resulting phosphobetaines from the reaction product obtained.

The novel phosphobetaines of the present invention are obtained in the form of colorless, thermally stable and highly viscous liquids.

A highly unexpected result resides in the fact that the present reaction of the formula IV α,β-unsaturated carboxylic acid esters entails substantially no side reactions, e.g. polymerization or formation of phosphine alkylenes and secondary products.

A further highly unexpected result resides in the fact that the reaction is easy to effect in a single reaction stage without any need to separate a tertiary phosphine intermediate or hydrolyze a carboxylic acid ester group to the carboxylate group, and with the resultant formation of high yields of desirable phosphobetaines. The reaction should preferably be effected in the presence of a catalyst.

The useful catalysts primarily comprise chlorides, sulfates and acetates of metals, such as cadmium, nickel and cobalt. The catalyst should conveniently be used at a rate of 0.1 to 10 millimol, preferably 1 to 5 millimol, based on the total mixture. It is also preferable to effect the reaction at temperatures of 0° to 120° C, more preferably 15° to 80° C.

Apart from water, the reaction mixture may contain one or more further solvents which primarily include alcohols or acetonitrile. It is finally advantageous to effect the reaction under inert gas, e.g. nitrogen.

The phosphobetaines obtained by the process of this invention are very pure (98–99%). They are obtained in good yields after distillative removal of the water or water/solvent-mixture.

The quantitative ratio of the reaction components is variable within wide limits and does not materially influence the course of the reaction. It is good practice, however, to use the formula III and formula IV reactants in the stoichiometric proportions necessary for the formation of the formula I phosphobetaines.

In accordance with an advantageous feature of the present process the formula IV α,β-unsaturated carboxylic acid ester is introduced together with the catalyst into an aqueous phase, which may be water or a water/solvent-mixture, the formula III phosphine is added thereto, the whole is reacted at 0° to 120° C, the resulting reaction solution is allowed to stand for a period of 2 to 3 hours, and the phosphobetaine is separated from the solvent.

The process of the present invention compares very favorably with the prior art methods, principally in respect of the following points: It is a single stage reaction, which is easy to carry out without any need to isolate intermediates, and it produces readily separable, uniform and very pure final products in good yields.

The only by-product obtained is the alcohol (corresponding to the formula IV compound) which can be separated together with the solvent.

The products of the present invention are, for example, suitable for use in imparting antistatic properties to textile materials, and for use as flame-proofing agents in foamed polyurethanes.

EXAMPLE 1

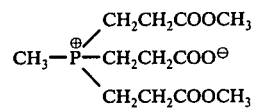

An agitator-provided apparatus scavenged with nitrogen was charged with 87 g (1 mol) of methyl acrylate in 200 ml of water and with 1 g of CdCl$_2$. 2½ H$_2$O. 20 g (0.4 mol) of methylphosphine was added together with nitrogen as an inert gas within 1 hour. The temperature was kept within the range of 24 to 30° C by cooling from the outside. An intermediate precipitate became completely dissolved during the post reaction period of 3 hours. The solvent was distillatively separated and a colorless highly viscous liquid remained behind. The yield was 90% of the theoretical.

| Analysis: | Found: | Calculated: |
|---|---|---|
| P | 9.9 % | 10.6 % |

EXAMPLE 2

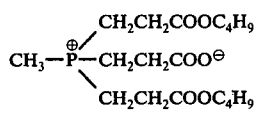

Butyl acrylate was reacted with methylphosphine in the manner described in Example 1. The yield was 97%.

| Analysis: | Found: | Calculated: |
|---|---|---|
| P | 8.0 % | 8.23 % |

EXAMPLE 3

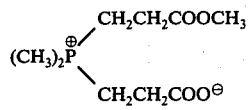

103 g (1.2 mol) of methyl acrylate in 200 ml of water was reacted as described in Example 1 with 38.5 g (0.62 mol) of dimethylphosphine in the presence of 0.5 g of CdCl$_2$. 2½ H$_2$O. The solvent and low-boiling fractions were distilled off and a highly viscous oil was obtained. The yield was 96% of the theoretical.

| Analysis: | Found: | Calculated: |
|---|---|---|
| P | 13.5 % | 14.06 % |

EXAMPLE 4

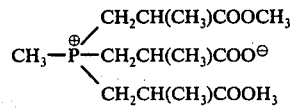

100 g (1 mol) of methyl methacrylate was reacted with 20 g (0.4 mol) of methylphosphine, in the manner described in Example 1. The yield was 86%.

| Analysis: | Found: | Calculated: |
|---|---|---|
| P | 8.8 % | 9.26 % |

EXAMPLE 5

The product of Example 1 was tested for its flame-retardant efficiency. To this end, it was incorporated into polyurethane soft foams and the foams were subjected to burn-up test ASTM D 1962-68.

More specifically, the following substances were intimately mixed together at room temperature:
200 g of a polyetherpolyol produced from glycerol and ethylene oxide with an OH-number of 46 mg KOH/g
7.0 g of water
0.4 g of NIOX Catalyst A 1 (a commercially available product of Union Carbide Corporation)
0.42 g of tin-II-octoate
2.0 g of SILICONE oil L 520 (a commercially available product of Union Carbide Corporation), and
14.0 g of the compound of Example 1.

Next, 92 g of toluylene diisocyanate was added with rapid agitation and the resulting reaction mixture was poured after 15 seconds in a plastics container, in which it was allowed to foam. The material ceased to rise after a maximum period of 2.5 minutes. After 24 hours, the foam was subjected to ASTM test D 1962-68.

The following result was obtained:
Standard foam (free from product of Example 1): Burning rate: 230 mm/min
Foam with product of Example 1: Burning rate: 86 mm/min.

EXAMPLE 6

Pre-mixtures of polymethane rigid foams containing the compound of Example 1 were tested as to storage life. To this end, the following substances were mixed together:
100 g of CARADOL 520, a polyol with an OH-number of 520 mg KOH/g (a commercially available product of Shell Company).
1 g of water,
1 g of SILICONE oil SF 1066 (a commercially available product of General Electric Company),
3 g of triethylamine,
24 g of trichlorofluoromethane, and
15 g of the compound of Example 1.

(a) The pre-mixture so made was immediately admixed with 150 g of diphenylene-4,4-diisocyanate and allowed to foam.
period of rise: 74 seconds. Height of foam: 17 cm.
(b) The pre-mixture was stored over a 6 month period at 22° C. After that storage period, the pre-mixture was admixed with 150 g of diphenylene-4,4-diisocyanate and allowed to foam.
Period of rise: 74 seconds. Height of foam: 17 cm.

The pre-mixtures of polymethane rigid foams made with the compound of the present invention could not be found to undergo hydrolysis under the conditions described above.

We claim:

1. Phosphobetaines of the formula I

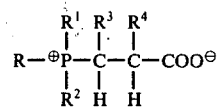

in which $R^1$ is methyl and $R^2$ has the meaning of $R^1$ or of R, R being a radical of the formula II

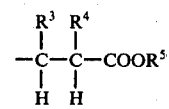

in which $R^3$ is hydrogen and $R^4$ is methyl or hydrogen, and $R^5$ is alkyl of 1–4 carbons.

2. Phosphobetaine of the formula

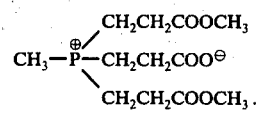

3. Phosphobetaine of the formula

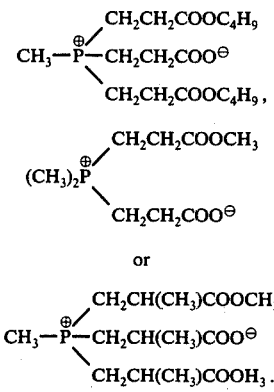

or

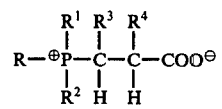

4. A process for making phosphobetaines of the formula

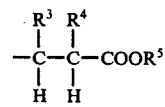

in which $R^1$ is methyl and $R^2$ has the meaning of $R^1$ or of R, R being a radical of the formula II

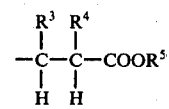

in which $R^3$ is hydrogen and $R^4$ is methyl or hydrogen, and $R^5$ is alkyl of 1–4 carbons, which process comprises reacting phosphines of the formula III

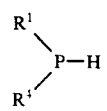

in which R¹ and R⁴ have the meanings given above, with an α,β-unsaturated carboxylic acid of the formula IV

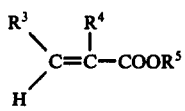   IV in which R³, R⁴ and R⁵ have the meanings given above, the reaction being effected in a single stage in the presence of water or a solvent/water-mixture, and separating the resulting phosphobetaines from the reaction product obtained.

5. The process as claimed in claim 4, wherein the reaction is effected in the presence of a catalyst.

6. The process as claimed in claim 5, wherein metal chlorides, sulfates or acetates are used as the catalyst.

7. The process as claimed in claim 6, wherein the catalyst is a chloride, sulfate or acetate of cadmium, nickel or cobalt.

8. The process as claimed in claim 5, wherein the catalyst is used at a rate of 0.1 to 10 millimol, based on the total mixture.

9. The process as claimed in claim 8, wherein the catalyst is used at a rate of 1 to 5 millimol, based on the total mixture.

10. The process as claimed in claim 4, wherein the reaction is effected at temperatures of 0° to 120° C.

11. The process as claimed in claim 10, wherein the reaction is effected at temperatures of 15° to 80° C.

12. The process as claimed in claim 4, wherein the solvent is an alcohol, acetonitrile or a mixture thereof.

13. The process as claimed in claim 4, wherein the phosphobetaine is separated from the reaction mixture by distillative removal of the solvent.

14. The process as claimed in claim 4, wherein the formula III phosphine and the formula IV α,β-unsaturated carboxylic acid ester are reacted in the stoichiometric proportions necessary for the formation of the formula I phosphobetaine.

15. The process as claimed in claim 4, wherein the formula IV α,β-unsaturated carboxylic acid ester is introduced together with the catalyst into an aqueous phase being water or a water/solvent-mixture, the formula III phosphine is added thereto, the whole is reacted at 0° to 120° C, the resulting reaction solution is allowed to stand for a period of 2 to 3 hours, and the phosphobetaine is separated from the solvent.

* * * * *